United States Patent
Gopichandran et al.

(10) Patent No.: US 10,293,029 B2
(45) Date of Patent: May 21, 2019

(54) EMBRYO IMPLANTATION

(71) Applicant: Ostara Biomedical Ltd, Liverpool, Merseyside (GB)

(72) Inventors: Nadia Gopichandran, Liverpool (GB); Nicolas Michel Orsi, Liverpool (GB); David Andrew Brooke, Liverpool (GB)

(73) Assignee: Ostara Biomedical Ltd., Leeds (GB)

(*) Notice: Subject to any disclaimer, the term of this patent is extended or adjusted under 35 U.S.C. 154(b) by 192 days.

(21) Appl. No.: 15/007,795

(22) Filed: Jan. 27, 2016

(65) Prior Publication Data
US 2016/0213749 A1    Jul. 28, 2016

Related U.S. Application Data

(60) Provisional application No. 62/108,222, filed on Jan. 27, 2015.

(30) Foreign Application Priority Data

Jan. 27, 2015    (GB) .................................. 1501302.2

(51) Int. Cl.
*A61K 38/20* (2006.01)
*A61D 19/02* (2006.01)
(Continued)

(52) U.S. Cl.
CPC .......... *A61K 38/208* (2013.01); *A61D 19/022* (2013.01); *A61D 19/04* (2013.01);
(Continued)

(58) Field of Classification Search
CPC .... A61K 38/208; A61K 38/193; A61K 38/19; A61K 9/0036; A61D 19/04; A61D 19/022
See application file for complete search history.

(56) References Cited

U.S. PATENT DOCUMENTS 6,258,998 B1    7/2001    Damiani
7,204,978 B1    4/2007    Robertson
(Continued)

FOREIGN PATENT DOCUMENTS

GB    1 393 628    5/1975
GB    2 003 386 A    3/1979
(Continued)

OTHER PUBLICATIONS

Seminal Fluid and Reproduction: much more than previously thought. Bromfield JJ. J Assist Reprod Genet (2014) 31:627-636. (published online May 17, 2014).*
(Continued)

*Primary Examiner* — Christine H Matthews
*Assistant Examiner* — Joshua Daryl D Lannu
(74) *Attorney, Agent, or Firm* — Stanek Lemon Crouse & Meeks, PA (57) ABSTRACT

The present invention relates to methods of and compositions comprising cytokines for, improving the success rate of embryo implantation and the success rate of pregnancy rates in females, by providing an immunopermissive uterine environment prior to insemination or implantation of embryos. The methods of the present invention are used to make the uterus more receptive or less hostile to, for example, transferred embryos, sperm or other allografted tissue.

15 Claims, 2 Drawing Sheets

(51) Int. Cl.
A61K 38/19 (2006.01)
A61D 19/04 (2006.01)
A61K 9/00 (2006.01)

(52) U.S. Cl.
CPC ............ *A61K 9/0036* (2013.01); *A61K 38/19* (2013.01); *A61K 38/193* (2013.01)

(56) References Cited

U.S. PATENT DOCUMENTS

| | | |
|---|---|---|
| 2005/0148023 A1 | 7/2005 | Thadhani |
| 2005/0272636 A1 | 12/2005 | Robertson |
| 2006/0002937 A1 | 1/2006 | Schwaeble |
| 2006/0008532 A1 | 1/2006 | Govardhan |
| 2006/0177459 A1 | 8/2006 | Robertson et al. |
| 2007/0178605 A1 | 8/2007 | Mor et al. |
| 2008/0233113 A1 | 9/2008 | Bansal |
| 2010/0093557 A1 | 4/2010 | Kumble |
| 2011/0212975 A1 | 9/2011 | Kao et al. |
| 2012/0115226 A1 | 5/2012 | Stachelsheid |
| 2015/0051441 A1 | 2/2015 | Gopichandran et al. |
| 2017/0095536 A1 | 4/2017 | Orsi et al. |

FOREIGN PATENT DOCUMENTS

| | | |
|---|---|---|
| GB | 2521709 A | 7/2015 |
| JP | 2009051827 A | 3/2009 |
| WO | WO 96/21427 | 7/1996 |
| WO | WO 98/39021 A1 | 9/1998 |
| WO | WO 00/25780 A1 | 5/2000 |
| WO | WO 00/68203 A1 | 11/2000 |
| WO | WO 01/19788 A2 | 3/2001 |
| WO | WO 01/64642 A2 | 9/2001 |
| WO | WO 01/64643 A2 | 9/2001 |
| WO | WO 02/00647 A1 | 1/2002 |
| WO | WO 03/007955 A2 | 1/2003 |
| WO | WO 03/064619 A2 | 8/2003 |
| WO | WO 2004/007472 A1 | 1/2004 |
| WO | WO 2004/026333 A1 | 4/2004 |
| WO | WO 2004/085385 A2 | 10/2004 |
| WO | WO 2005/017192 A3 | 2/2005 |
| WO | WO 2005/035717 A3 | 4/2005 |
| WO | WO 2005/115456 A2 | 12/2005 |
| WO | WO 2006/001463 A1 | 1/2006 |
| WO | WO 2007/011759 A2 | 1/2007 |
| WO | WO 2007/088996 A1 | 8/2007 |
| WO | WO 2007/088999 A1 | 8/2007 |
| WO | WO 2007/092353 A3 | 8/2007 |
| WO | WO 2007/113682 A3 | 10/2007 |
| WO | WO 2008/070902 A1 | 6/2008 |
| WO | WO 2008/073670 A2 | 6/2008 |
| WO | WO 2009/010455 A2 | 1/2009 |
| WO | WO 2009/010871 A2 | 1/2009 |
| WO | WO 2009/026717 A1 | 3/2009 |
| WO | WO 2009/051827 A1 | 3/2009 |
| WO | WO 2009/076618 A2 | 6/2009 |
| WO | WO 2009/125219 A3 | 10/2009 |
| WO | WO 2009/139784 A1 | 11/2009 |
| WO | WO 2010/048149 A1 | 4/2010 |
| WO | WO 2010/080537 A1 | 7/2010 |
| WO | WO 2010/126528 A1 | 11/2010 |
| WO | WO 2010/126553 A1 | 11/2010 |
| WO | WO 2011/015037 A1 | 2/2011 |
| WO | WO 2011/143752 A1 | 11/2011 |
| WO | WO 2011/159297 A1 | 12/2011 |
| WO | WO 2012/079032 A2 | 6/2012 |
| WO | WO 2012/080729 A2 | 6/2012 |
| WO | WO 2012/123745 A1 | 9/2012 |
| WO | WO 2013/093878 A1 | 6/2013 |
| WO | WO 2014/087218 A1 | 6/2014 |
| WO | WO 2015/022509 A1 | 2/2015 |
| WO | WO 2015/081157 A1 | 6/2015 |

OTHER PUBLICATIONS

Bromfield "Seminal fluid and reproduction: much more than previously thought", *J Assist Reprod Genet* 31:627-636 (2014).
Fraccaroli et al. "A potential tolerogenic immune mechanism in a trophoblast cell line through the activation of chemokine-induced T cell death and regulatory T cell modulation", *Human Reproduction* 24(1):166-175 (2009).
Gopichandran et al. "Multiplex determination of murine seminal fluid cytokine profiles", *Reproduction* 131:613-621 (2006).
Gui et al. "Effects of Acupuncture on LIF and IL-12 in Rats of Implantation Failure", *Am. J. Reprod. Immunol.* 37:383-390 (2012).
Orsi et al. "Uterine and serum cytokine arrays in the mouse during estrus", *Animal Reproduction Science* 100:301-310 (2007).
Ostanin et al. "Role of Cytokines in the Regulation of Reproductive Function", *Bulletin of Exp. Biology and Medicine* 143(1):75-79 (2007).
Schjenken et al. "Seminal Fluid and Immune Adaptation for Pregnancy—Comparative Biology in Mammalian Species", *Reprod. Dom. Anim.* 49(3):27-36 (2014).
Vujisic et al. "Ovarian follicular concentration of IL-12, IL-15, IL-18 and p40 subunit of IL-12 AND IL-23", *Human Reproduction* 21(10):2650-2655 (2006).
Zenclussen et al. "Questioning the Th1/Th2 Paradigm in Reproduction: Peripheral Levels of IL-12 are Down-Regulated in Miscarriage Patients", *AJRI* 48:245-251 (2002).
Search Report corresponding to British Application No. GB1501302.2 dated Oct. 22, 2015.
Notification of Transmittal of the International Search Report and the Written Opinion of the International Searching Authority, or the Declaration corresponding to International Application No. PCT/GB2016/050175 dated Apr. 13, 2016.
Bathini et al. "2-Aminoquinazoline inhibitors of cyclin-dependent kinases", *Bioorganic & Medicinal Chemistry Letters* 15:3881-3885 (2005).
Caballero et al. "2D Autocorrelation, CoMFA, and CoMSIA modeling of protein tyrosine kinases' inhibition by substituted pyrido[2,3-d]pyrimidine derivatives", *Bioorganic & Medicinal Chemistry Letters* 16:810-821 (2008).
Chaouat et al, "Immunoendocrine Networks in Pregnancy and Parturition," Regional Immunology, 1994, vol. 6, pp. 295-301.
De et al., "Expression of interleukin 1, interleukin 6 and tumour necrosis factor α in mouse uterus during the peri-implantation period of pregnancy," Journal of Reproduction and Fertility, Ltd., 1993, vol. 97, Issue 1, pp. 83-89.
Feinberg et al. "Transforming Growth Factor—β Stimulates Trophoblast Oncofetal Fibronectin Synthesis in Vitro: Implications for Trophoblast Implantation in Vivo", *J. Clinical Endocrinology and Metabolism*, 78(5):1241-1248 (1994.
Han et al., "Development of Luteinizing Hormone Releasing Hormone (LHRH) Delivery Systems for Vaginal Mucosal Route," Archives of Pharmaceutical Research, 18(5): 325-331 (1995).
Hansen et al., "Mastitis and Fertility in Cattle—Possible Involvement of Inflammation of Immune Activation in Embryonic Mortality," American Journal of Reproductive Immunology, 2004, vol. 51, pp. 294-301.
International Search Report and the Written Opinion of the International Searching Authority corresponding to International Application No. PCT/GB2016/053080 (11 pages), dated Jan. 25, 2017.
Kraus et al., "Peripheral Blood Cytokine Profiling During Pregnancy and Post-partum Periods," American Journal of Reproductive Immunology, 2010, vol. 64, Issue 6, pp. 411-426.
Mas et al., "Immune Regulation at the Interface During Early Steps of Murine Implantation: Involvement of Two New Cytokines of the IL-12 Family (IL-23 and IL-27) and of TWEAK," American Journal of Reproductive Immunology, 2003, vol. 59, Issue 4, pp. 323-338.
Notification of Transmittal of the International Search Report and the Written Opinion of the International Searching Authority, or the Declaration corresponding to International Application No. PCT/GB2014/052450 dated Oct. 27, 2014.
Okada et al, "Vaginal Absorption of a Potent Luteinizing Hormone-Releasing Hormone Analog (Leuprolide) in Rats I; Absorption by (56) References Cited

OTHER PUBLICATIONS

Various Routes and Absorption Enhancement," Journal of Pharmaceutical Sciences, 71(12): 1367-1371 (1982).
Orsi et al., "Cytokine Networks and the Regulation of Uterine Function in Pregnancy and Parturition," Journal of Neuroendocrinology, 2008, vol. 20, pp. 462-469.
Ota et al., "Expression of a2 Vacuolar ATPase in Spermatozoa is Associated with Semen Quality and Chemokine-Cytokine Profiles in Infertile Men," PLoS ONE, Jul. 2013, vol. 8, Issue 7, pp. 1-7.
Search Report under Section 17 corresponding to British Application No. GB1417607.7 (2 pages), dated Mar. 13, 2015.
Search Report under Section 17(5) corresponding to British Application No. GB1314452.2 dated Jan. 7, 2014.
Search Report under Section 17(5) corresponding to British Application No. GB1414258.2 dated Apr. 28, 2015.
Search Report under Section 17(6) corresponding to British Application No. GB1314452.2 dated May 22, 2014.
Shuya et al, "Leukemia Inhibitory Factor Enhances Endometrial Stromal Cell Decidualization in Humans and Mice," PLoS ONE, Sep. 2011, vol. 6, Issue 9, pp. 1-11.
Svensson et al., "Macrophages at the Fetal-Maternal Interface Express Markers of Alternative Activation and Are Induced by M-CSF and IL-10," The Journal of Immunology, 2011, vol. 187, pp. 3617-3682.
Torchinsky et al., "TNF-α acts to prevent occurrence of malformed fetuses in diabetic mice," Diabetologia, 2004, vol. 47. pp. 132-139.
Zollner et al., "LIF and TNF alpha concentrations in embryo culture media are predictive for embryo implantation in IVF," Asian Pacific Journal of Reproduction, 2012, vol. 1, No. 4, pp. 277-282.
Search Report, GB Application No. 1 616 851.0, dated Jul. 24, 2017, 5 pages.

\* cited by examiner

EMBRYO IMPLANTATION

RELATED APPLICATIONS

This application claims priority to British Application No. GB 1501302.2, filed on Jan. 27, 2015 and U.S. Provisional Application No. 62/108,222, filed on Jan. 27, 2015. The contents of each of these applications are incorporated herein by reference in their entireties.

FIELD

The present invention relates to methods of and compositions for, improving the success rate of embryo implantation and the success rate of pregnancy in females, by providing an immunopermissive uterine environment prior to insemination or implantation of embryos. The methods of the present invention are used to make the uterus more receptive or less hostile to, for example, transferred embryos, sperm or other allografted tissue. The invention also includes inter alia compositions and formulations for use in the methods of the invention.

BACKGROUND

The uterine environment, which, if hostile/non-receptive, can be responsible for poor implantation rates of good quality embryos in human and animals alike. It is believed that an inadequately primed uterine environment may also be responsible for many cases of reproductive failure in terms of failed implantation and spontaneous abortion. Similarly, a failure in uterine priming is recognised in humans as being causative to pregnancy complications such as pre-eclampsia and foetal growth restriction by preventing appropriate placental development.

Genetically altered or modified animals provide valuable models for testing novel gene and drug therapies in vivo and are the main reason the numbers of animal experiments have been rising in the last decade. In the UK, over four times as many scientific procedures using genetically modified animals were carried out in 2011 as compared to 1995. The use of genetically modified animals now represents over 50% of all scientific procedures on animals. The largest category of use is breeding (to produce genetically modified animals), with rodents accounting for almost 1.8 million procedures in the UK in 2012 alone, on a background trend for this number to increase annually. Embryo transfer in rodents underpins the development of transgenic approaches, re-derivation of specific strains and facilitates the transport of animal-lines across large distances. Typically, embryo transfer requires induction of pseudopregnancy in recipient females. This phenomenon prepares the uterus for implanting embryos, however, the success rate of transferring genetically modified embryos, despite induction of pseudopregnancy, remains relatively low.

Mice are spontaneous ovulators and can become pseudopregnant following an estrus in which the female is mated with a genetically sterile male such as the T145H-Re strain (which is sterile due to a chromosomal translocation) obtainable from Harlan Laboratories Inc or a vasectomised male. Both sets of males ejaculate seminal plasma devoid of functional sperm. However, both genetically sterile and vasectomised mice are relatively costly. In the instance of vasectomised males, sterility cannot be guaranteed to be 100% effective and needs testing for each male, while the production of genetically sterile males generates unwanted surplus females.

Alternatively, pseudopregnancy can be induced by simulating the normal vaginal stimuli attained by mating with artificial mechanical stimulation, for example by a vibrating engraving tool (Kenney et al; *J Reprod. Fert.* 1977, 49, 305-309). It was found that the number and rate of intromissions were crucial influences on reproductive success (Diamond; *Science,* 1970, 169, 4, 995-997). Whilst this approach has seen some success in rats and mice mechanical stimulation had no effect on the induction of pseudopregnancy in the Golden Hamster (Diamond et al *J. Reprod. Fert.* 1968, 17, 165-168). When the female is mated with an infertile male or mechanically stimulated, the corpus luteum persists without an embryo, leading to pseudopregnancy. The female will develop mammary glands, lactate and build nests in the pseudopregnant state. There is a need to improve the methods of inducing a pseudopregnant state in laboratory test animals.

Although the protocols for embryo transfer in an array of rodent species are relatively well-established, their poor optimization means that there is a significant wastage of animals, raising a number of financial and ethical issues in animal units worldwide. The prior art standard approach currently relies on mating recipient females with vasectomised males to induce pseudopregnancy rather than mechanical stimulation, where copulatory activity and seminal exposure of the maternal reproductive tract triggers a neuroendocrine and localised (to the uterus, principally) inflammatory response involving a complex cascade of cytokine and prostaglandin-mediated events geared towards creating an immunopermissive environment in the uterus, thereby favouring pre-implantation embryo development and/or blastocyst implantation and the establishment of pregnancy. Even in the absence of fertilisation, luteal development and progesterone production are supported, and the maternal physiology is orchestrated to render the uterus receptive to transferred embryos for up to 10-13 days. This technique is routinely used to support the development of normal (cryopreserved strain regeneration/re-derivation) or genetically modified (transgenic/chimaeric/cloned) embryos.

However, the efficacy of this approach is limited. Typically, four times as many females are prepared for the procedure compared to those becoming pregnant. When implanting fresh or frozen embryos this represents a considerable wastage of valuable biological material and effort. Moreover, numbers of young vasectomised males also need to be maintained alongside the prospective recipients: these can only mate 2-3 times a week and are typically replaced every 6-9 months in order to maintain performance.

Mating predominantly occurs when the recipient female is in estrus. The estrus cycle lasts 4-5 days in the mouse and rat (equivalent to a woman's average 28 day menstrual cycle), which leads to the need to rely on a large pool of potential recipient females to take part in potential matings with vasectomised or otherwise sterile males. Typically, 75% of recipients are not in estrus in randomly cycling populations, leading to large numbers of females and vasectomised or otherwise sterile males being kept and, in the case of the former, often not used as surrogates in order to guarantee adequate numbers of recipients for use in timed transfers. This is particularly evident in instances where the embryos to be transferred are particularly valuable. Improvements to this approach have relied on timed estrus induction via the Whitten effect in recipient females. This strategy relies on pheremonal stimulation of recipient females, which typically brings them into estrus 3 days after exposure to stud male urine-soiled bedding. However, the cycling stage of females at the time of pheremonal exposure, proximity to stud cages and the age of recipients can all have adverse effects on the reliability of this approach, making it relatively inefficient.

The chances of females being in estrus (sexually receptive) at the right time is 1:4 due to the length of their cycle (4 days). Thus, if 4 recipients are required, 16 females will be mated to 16 males, which translates to a 25% success rate. This figure can be even lower as some females will refuse to mate with their partner. The key point is that although most breeders either select females in estrus, or induce estrus before mating with sterile males, still only a relatively low percentage (often about 50%—but as low as 15% in some facilities) of oestrus females will become 'plugged' and so assumed to be pseudopregnant. Furthermore, females also have a very limited functional lifespan of a few months of age as embryo transfer recipients. Females rapidly accumulate abdominal fat as they mature, making laparotomic embryo transfers (the most common and successful method) technically too challenging.

It is known that seminal fluid ejaculate is a complex mixture rich a variety of cytokines and prostaglandins, and that some of the cytokines may have a positive effect on the vaginal/uterine environment and others may have deleterious effects which both and ultimately affect receptivity to embryo implantation. For example, the pro-inflammatory cytokine GM-CSF (CSF-2) is present in seminal fluid ejaculate and is also known to be released by endometrial epithelial cells in response to seminal plasma within hours of coitus (Robertson et al. Reprod Fertil Dev, 1990. 2(4): p. 359-68) and that maternal GM-CSF is required for foetal viability and growth (Robertson et al. Biology of Reproduction Feb. 1, 1999 vol. 60 no. 2 251-261). Furthermore WO1999067364 A1 discloses media supplemented with GM-CSF to promote blastocyst growth and WO 2014087218 describes GM-CSF as sole acting substance to prevent recurrent miscarriage.

The cytokine IL-12 is also present in seminal fluid ejaculate and has been shown to be deleterious to pregnancy (Reina et al. Am J Reprod Immunol. 2004 May; 51(5):345-51) and to be abortifacient in high concentrations, particularly in synergy with IL-18 and IL-2, via activation of maternal lymphocytes (Hayakawa et al. Am J Reprod Immunol. 1999; 41: 320-329). Other studies have shown that IL-12 injections (100 ng i.p. daily on days 5, 6, 7 and 8 of pregnancy) into CBA/J mice caused increased abortion rate when compared to controls (Zenclussen et al Scand J Immunol. 2002 June; 55(6):560-9).

By the compositions and methods of the present invention it is envisaged that the need for vasectomised or otherwise sterile male mice can be dramatically reduced along with a significant reduction of female mice usage.

The present invention aims to improve the pregnancy rates in mammalian females in terms of established pregnancies and/or increased litter number following artificial or natural insemination or following transplantation of fresh or frozen or otherwise preserved embryos.

BRIEF SUMMARY OF THE DISCLOSURE

The present invention resides in the use of IL-12 for improving pregnancy rates and/or for reducing maternal alloreactivity against seminal fluid/sperm or embryos or other allograft tissue and/or for providing an immunopermissive uterine environment in females prior to implantation of an embryo or prior to insemination.

According to a first aspect of the invention there is provided a composition of matter for use in improving pregnancy rates and/or for reducing maternal alloreactivity against seminal fluid/sperm or embryos or other allograft tissue and/or for providing an immunopermissive uterine environment in females prior to implantation of an embryo or prior to insemination, the composition comprising IL-I2.

Preferably, the IL-12 is either IL-12 p40 or IL-12p70.

Preferably, the composition further includes GM-CSF.

Preferably, the composition further includes any one two or three of TGFβ, Eotaxin and RANTES.

Preferably, the composition further includes any one, two, three, four, five six or seven additional cytokines selected from the group comprising MIP, G-CSF, MCP-1, IL-17, 1L-13, IL-9 and TNF-α.

It is within the scope of the invention to provide a number of specific combinations of the specified cytokines using the basic IL-12 and a further, for example and without limitation GM-CSF combination, or IL-12, eotaxin and RANTES combination, with or without additional further cytokines for use in inducing a uterus to be more receptive or less hostile to transferred embryo, sperm or other allografted tissue.

Accordingly the compositions of the present invention may include a variety of multiple cytokines as it is recognised that high concentrations of a specific cytokine in seminal fluid do not necessarily reflect their biological significance.

Preferably, the composition of the first aspect of the invention further includes any one or more of the additional cytokines selected from the group comprising IL-1α, IL-1β, IL-1ra, IL-2ra, IL-2, IL-3, IL-4, IL-5, IL-6, IL-7, IL-8, IL10, IL-15, IL-16, IL-18, FGF, IFN-α2, IFN-γ, IP-10, PDGF, VEGF, CTACK, KC, GROα, HGF, ICAM-1, LIF, MCP-3, M-CSF, MIF, MIG, β-NGF, SCF, SCGF-β, SDF-1α, TNF-β, TRAIL and VCAM-1.

Table 1 below lists the acronyms for cytokines referred to in the present invention:

TABLE 1

| Cytokines analysed using bio-plex assays | |
|---|---|
| IL-1α | Interleukin-1α |
| IL-1β | Interleukin-1β |
| IL-1ra | Interleukin-1 receptor antagonist |
| IL-2ra | Interleukin-2 receptor antagonist |
| IL-2 | Interleukin-2 |
| IL-3 | Interleukin-3 |
| IL-4 | Interleukin-4 |
| IL-5 | Interleukin-5 |
| IL-6 | Interleukin-6 |
| IL-7 | Interleukin-7 |
| IL-8 | Interleukin-8 |
| IL-9 | Interleukin-9 |
| IL-10 | Interleukin-10 |
| IL12 (p40) | Interleukin-12 (p40) |
| IL-12 (p70) | Interleukin-12 (p70) |
| IL-13 | Interleukin-13 |
| IL-15 | Interleukin-15 |
| IL-16 | Interleukin-16 |
| IL-17 | Interleukin-17 |
| IL-18 | Interleukin-18 |
| Eotaxin | Eotaxin |
| FGF | Basic fibroblast growth factor |
| G-CSF | Granulocyte-colony stimulating factor |
| GM-CSF | Granulocyte macrophage-colony stimulating factor |
| IFN-α 2 | Interferon-α2 |
| IFN-γ | Interferon-γ |
| IP-10 | IFN-γ inducible protein-10 |
| LEPTIN | Hormone associated with weight control |
| MCP-1 | Macrophage chemotactic protein-1 |

TABLE 1-continued

Cytokines analysed using bio-plex assays

| | |
|---|---|
| MIP-1α | Macrophage inflammatory protein-1α |
| MIP-1β | Macrophage inflammatory protein-1β |
| PDGF | Platelet derived growth factor |
| RANTES | Regulated upon activation normal T cell expressed and secreted |
| TNF-α | Tumour necrosis factor |
| VEGF | Vascular endothelial growth factor |
| CTACK | Cutaneous T cell attracting chemokine |
| KC | Ketatinocyte derived cytokine |
| GROα | Growth regulated ongogene-α |
| HGF | Hepatocyte growth factor |
| ICAM 1 | Intercellular cell adhesion molecule |
| LIF | Leukaemia inhibitory factor |
| MCP3 | Monocyte chemoattractant protein-3 |
| M-CSF | Macrophage-colony stimulating factor |
| MIF | Macrophage migration inhibitory factor |
| MIG | Monokine induced by IFN-γ |
| β-NGF | Basic-nerve growth factor |
| SCF | Stem cell factor |
| SCGF-β | Stem cell growth factor-β |
| SDF-1α | Stromal cell derived factor-1α |
| TGF-β1 | Transforming growth factor β1 |
| TNF-β | Tumour necrosis factor-β |
| TRAIL | Tumour necrosis factor related apoptosis inducing ligand |
| VCAM-1 | Vascular cell adhesion molecule-1 |

The present invention resides in harnessing the properties of seminal agents which promote uterine receptivity and in providing a chemicophysical alternative to vasectomised or otherwise sterile males, preferably in the form of a vaginal insert such as a pessary, gel, spray or allied to any other dissolvable carrier.

The present invention, advantageously, given that the demand for transgenic non-human animal models is set to rise further, provides an alternative to vasectomised or otherwise sterile males inducing pseudopregnancy and also advantageously reduces the number of females required by improving uterine receptivity to transferred embryos.

The present invention advantageously obviates the need for vasectomised or otherwise sterile males given that their contribution solely relates to triggering the neuroendocrine and uterine inflammatory responses required to induce pseudopregnancy.

According to a further aspect of the invention there is provided a pharmaceutical composition comprising the cytokines as herein before described in the form of a vaginal insert or an intra-uterine device for improving pregnancy rates and/or for reducing maternal alloreactivity against seminal fluid/sperm or embryos or other allograft tissue and/or for providing an immunopermissive uterine environment in females prior to implantation of an embryo or prior to insemination.

Preferably, the female is mammalian and more preferably is human.

Preferably, the mammalian female is selected from the group comprising mouse, rat, rabbit, gerbil, guinea pig, hamster, primate (monkey, ape), canine, feline, porcine or any other laboratory animal or endangered species into which embryos are placed.

Preferably, the female is a mammal and more preferably still is a rare breed/species or a breed/species that is endangered.

Preferably, the female may be selected from the group comprising animals the orders of Artiodactyla, Carnivora, Cetacea, Chiroptera, Dermoptera, Edentata, Hyracoidae, Insectivora, Lagomorpha, Marsupialia, Perissodactyla, Pholidata, Pinnipedia, Primates, Proboscidea, Rodentia, Sirenia and Tubulidentata.

Preferably, the amount of any one of the cytokines present in the composition is released, from any one of its deliverable forms as described herein after, in situ either above or within their approximate physiological range found in seminal fluid.

Cytokines are measured as pg/ml as the standardised recognised values in the art.

The present invention resides in harnessing the properties of seminal agents, especially cytokines (which are protein modulators of the immune response and which promote uterine receptivity), by providing a chemicophysical formulation preferably in a form suitable for vaginal delivery for insertion into the female prior to mating/insemination or prior to implantation of embryos. The introduced formulation releases agents which enhance the receptivity of the uterine environment.

The approach used in the present invention is to mimic the biochemical signalling mediated by seminal plasma by using a pessary-based, gel-based, solution-based, emulsion-based, powder-based or aerosol-based delivery system. Pessaries are already routinely used in an array of large domestic species (e.g. cattle) for the synchronisation of estrous cyclicity for embryo transfer/artificial insemination. However, to date, no pessary has been used with the compositions of the present invention or for the specified function of promoting uterine receptivity and/or inducing a pseudopregnant state.

Preferably, the cytokines are recombinant. That is to say that they are made by genetically engineering a bacterium or other cell type using recombinant technology.

The present invention provides compositions for females comprising recombinant cytokine preparations, typically in the form of a pessary placed in the vagina or an aerosol foam released in the vagina prior to insemination/embryo transfer in order to reduce maternal immune alloreactivity against sperm/embryos, thereby improving pregnancy rate/outcome. The use of this mode of delivery as a strategy for improving endometrial receptivity is novel.

Preferably, the composition further includes adjuvants such as preservatives, anti-oxidants, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. It may also be beneficial to include waxes, water and co-solvents.

Preferably the composition is in a form suitable for vaginal delivery such as a vaginal capsule, vaginal gel, vaginal tablet, vaginal powder, vaginal solution, vaginal pessary, vaginal cup, vaginal sponge or vaginal foam or spray. Most preferably the composition is in the form of a vaginal pessary.

Preferably, the vaginal formulation is dissolving or non-dissolving, degradable or non-degradable.

Preferably, the compositions of the present invention are prepared as a vaginal suppository, tablet, powder, bioadhesive tablet, capsule, microparticle, bioadhesive microparticle, microcapsule, microsphere, liposome, cream, lotion, foam, spray, film, ointment, solution, gel, or a sustained release gel, tablet or capsule, or a sustained release suppository administered to the vagina or incorporated into a vaginal device.

In an alternative embodiment of the invention the compositions of the present invention are prepared for oral or rectal administration or as an enteric coated tablet for use in gastrointestinal tract delivery so that they may be absorbed from the mucosa of the gastrointestinal tract. The rationale for these modes of administration is that the mucosal immune system in the digestive system is linked to that of the reproductive tract. In this way, mucosal priming will occur, thereby facilitating embryo implantation, allograft/gamete/embryo tolerance, self-immunotolerance or tolerance of the endogenous/exogenous microflora of both the reproductive and digestive tracts.

Preferably, the compositions of the present invention are prepared as multiwalled, multicored, microencapsulated preparations. More preferably, the active components of the composition are when used as dried material encapsulated in a shell/coat like a gelatin capsule.

Compositions for vaginal administration are preferably prepared by mixing the compositions of the present invention with suitable pharmaceutical ingredients or non-irritating excipients or carriers such as cocoa butter, polyethylene glycol or a suppository wax which are solid at room temperature but liquid at body temperature and therefore melt in the rectum or vaginal cavity and release the active compound. A typical example of a vaginal pessary would include the active ingredients and the following excipients: medium chain tryglycerides and hard fat.

Alternatively, the composition can be incorporated into an intravaginal device or a coating of such device, for example, a tampon or tampon-like device coating, or incorporated into a sponge, foam, strip, powder, pessary, or other material. Absorbent material or matrix of such devices may be impregnated with a composition of the present invention as a liquid solution, suspension lotion, powder, cream, microemulsions or suspension of liposomes, bioadhesive nanoparticles, or bioadhesive microparticles. Preferably, the vaginal device is dissolving or non-dissolving, degradable or non-degradable.

Preferably, the compositions further include a mucoadhesive agent, sorption promoter or penetration enhancer. The compositions of the present invention are delivered by transmucosal vaginal delivery and comprise contacting the vaginal mucosa with the compositions of the present invention.

Preferably, the compositions for vaginal delivery are for rapid delivery, controlled delivery, continuous delivery or pulsed delivery.

It is envisaged that the composition of the present invention will be formulated in one embodiment as a pessary with a slow wax melt or a fast wax melt to achieve continuous or rapid delivery respectively. In an alternative embodiment, the composition of the invention will be formulated into a foam or gel with appropriate additives to permit controlled release.

Preferably, in the instance of providing the composition of the present invention as a vaginal pessary, tablet, bioadhesive tablet, capsule, powder, microparticle, bioadhesive microparticle, that the coating will be abrasive. This is an appropriate modification to the deliverable composition, especially if the penis of the male of the species to be prepared for uterine receptivity has a rough epidermis, keratinous spines, etc. In this instance it is desirable for the inserted vaginal delivery vehicle to have a rough outer coating similar to that as on the penis in order to elicit a maternal inflammatory response to improve penetration of the preparation into the mucosa, elicit an initial inflammatory response and aid generic neuroendocrine stimulation.

In a particularly preferred embodiment of the invention the composition is in the form of a pessary. Preferably the pessary is suitably sized and shaped so as to be inserted into the vagina of the female. The pessary may have a solid core and an outer porous layer. Typical dimensions of a pessary for mice are overall diameter of 4 mm and a length of 7 mm. The diameter and length of the pessary is dependent upon the size of the vagina of the species into which it is inserted, it is desirous that the pessary be sized and shaped so that when inserted into the vagina it is retained without discomfort.

According to a further aspect of the invention there is provided the composition of the first aspect of the invention for the manufacture of a medicament for improving pregnancy rates and/or reducing maternal alloreactivity against seminal fluid/sperm or embryos or other allograft tissue and/or for providing an immunopermissive uterine environment in females prior to implantation of an embryo or prior to insemination.

According to a further aspect of the invention there is provided a method of reducing maternal alloreactivity in a non-human female mammal against seminal fluid/sperm, embryos or other allograft (including existing microflora) comprising exposing the vaginal/gastrointestinal tract mucosa to a composition as hereinbefore described, the method comprising:
(i) introducing at least one vaginal delivery vehicle comprising the composition of the present invention into the vagina of the female;
(ii) optionally inserting further vaginal delivery vehicle(s);
(iii) allowing a sufficient period of time to elapse to allow the active components of the vaginal delivery vehicle to be released and to penetrate into the vagina and be absorbed transmucosally and/or diffuse and/or be transported into the uterus and/or through the gastrointestinal tract mucosa; and
(iv) inseminating the female by either mating with a male or by artificial insemination, donor gametes or introducing an embryo or other allograft into the uterus for implantation.

According to further aspect of the invention there is provided a method of improving pregnancy rate or outcome in a non-human female mammal prior to insemination or implantation of an embryo comprising exposing the vaginal/gastrointestinal tract mucosa to a composition as hereinbefore described, the method comprising:
(i) introducing at least one vaginal delivery vehicle comprising the compositions of the present invention into the vagina of the female;
(ii) optionally inserting further vaginal delivery vehicle(s);
(iii) allowing a sufficient period of time to elapse to allow the active components of the vaginal delivery vehicle to be released and to penetrate into the vagina and be absorbed transmucosally and/or diffuse and/or be transported into the uterus and/or through the gastrointestinal tract mucosa; and
(iv) inseminating the female by either mating with a male or by artificial insemination, donor gametes or introducing an embryo or other allograft into the uterus for implantation.

In a further embodiment of the invention, steps (iii) and (iv) are performed simultaneously/close chronological sequence in the case of artificial or natural insemination. The methods of the invention uses a composition comprising recombinant cytokine-containing pessaries, gel, spray or foam placed in the vagina at the time of insemination/embryo transfer to reduce maternal immune alloreactivity against sperm/embryos/gametes and endogenous or exogenous microflora, thereby improving pregnancy rate.

The number of doses and period between doses can be varied according to requirements and may vary depending on species or breed, super/ovulation status, seasonal effect, lactational status and number of previous failed pregnancies or previous inseminations or IVF treatments. It may also vary depending on maternal age and whether the female is primigravida.

Preferably, the methods of the invention when used for laboratory non-human animals further includes the step of synchronizing estrus in recipient females.

According to a yet further aspect of the invention there is provided a kit of parts and optionally a set of written instructions therefore, the kit comprising a number of vaginal delivery vehicles containing the compositions of the invention and an apparatus for inserting said vaginal delivery vehicles into the vagina of the recipient non-human female mammal.

It will be appreciated that features described for the first aspect of the invention are equally applicable to each and all aspects of the invention and apply mutatis mutandis.

The invention will be described by way of example only with reference to the following figures wherein:

BRIEF DESCRIPTION OF THE DRAWINGS

Embodiments of the invention are further described hereinafter with reference to the accompanying drawings, in which:

FIG. 1 shows the Bayesian mathematical modelling of cytokine networks in mouse seminal plasma. The nodes (cytokines) are colour-coded according to the conditional probability of corresponding mediator relative concentrations being high (green), low (red) or medium (white) concentration given the state(s) of their parent nodes (the bar charts adjacent to each node reflect underlying conditional probabilities of categorization into one of the three concentration bins from low on the left to high on the right). The normalized concentration (low or high) determines the intensity of the node colour. Edges (causal connecting lines between nodes) represent causal directed interactions between nodes. These cytokines will interact with the maternal reproductive tract to induce immunopermissiveness to paternal antigens.

DETAILED DESCRIPTION

Figure 1:
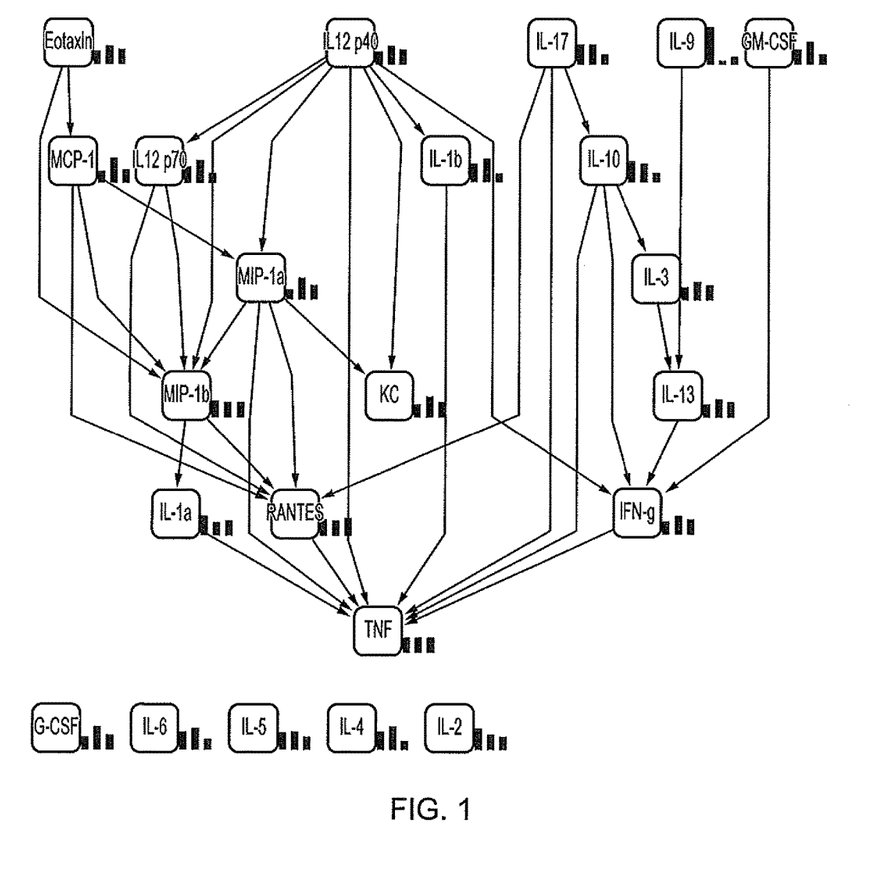
Figure 2:
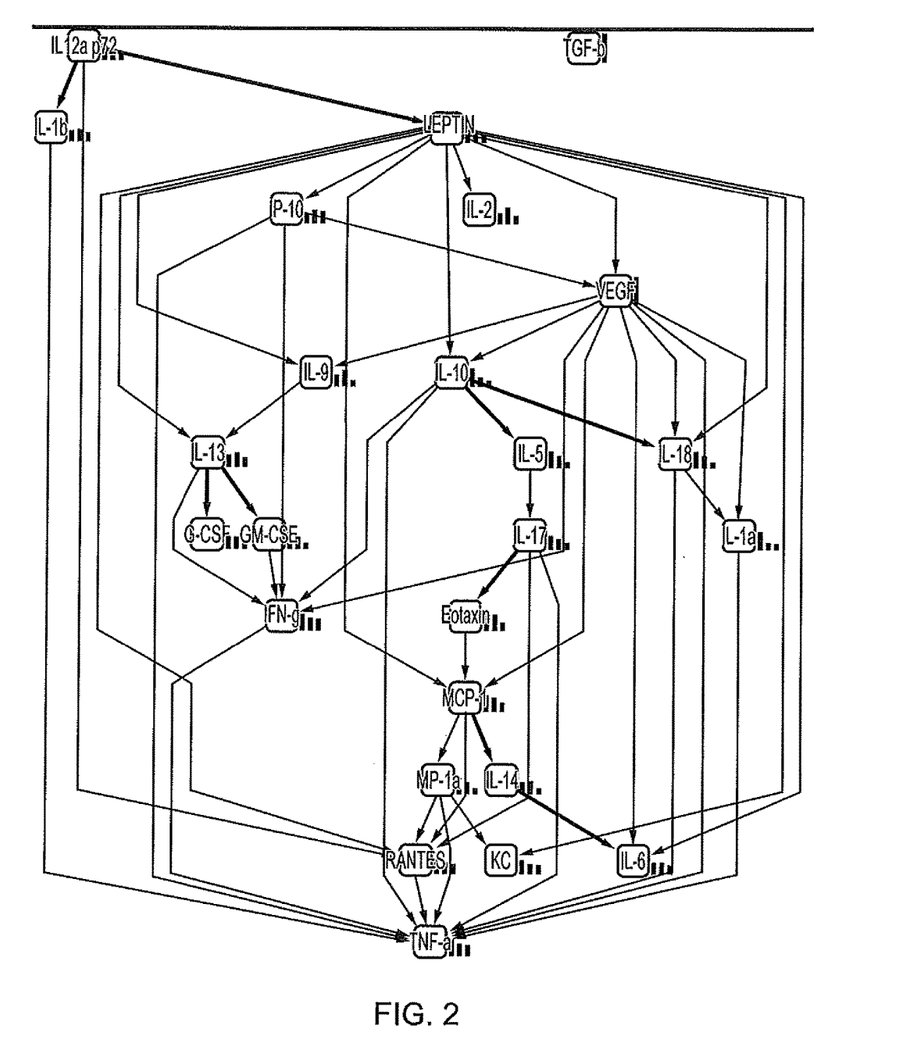
FIG. 2 shows the Bayesian mathematical modelling of cytokine networks in rat seminal plasma (details discussed above). Very high confidence level edges are coloured in red, based upon the confidence analysis of the Bayesian result (based on occurrence in >90% bootstrapping iterations).

Reference herein to "embryo" is intended to include a blastula, blastocyst, fertilized ovum or an organism in its early stages of development, especially before it has reached a distinctively recognizable form that is to be implanted into a female recipient.

Reference herein to an "improved pregnancy rate" is intended to include a positive pregnancy outcome or improved perinatal survival or general viability following artificial insemination with processed semen or natural insemination or following transplantation of fresh or frozen or otherwise preserved embryos. The term pregnancy as used hereinafter is to be interpreted as encompassing a pregnancy resulting from natural or artificial insemination or following transplantation of a fresh or frozen or otherwise preserved embryo(s) and gametes.

Reference herein to a "vaginal insert" or an "intra-uterine device" is intended to include any pessary-based, gel-based, solution-based, emulsion-based, powder-based or aerosol-based delivery system that is capable of delivering the compositions of the present invention into the vagina so as to permit the compositions of the present invention to have a pharmacological effect on the vaginal/uterine environment.

Reference herein to a "pessary" is intended as a means of delivery of the pharmaceutical substances of the present invention so that they are easily absorbed through the mucosal surfaces of the vagina, or intended to have action in the locality, for example against inflammation, or on the uterus.

"Pharmaceutical ingredient" or "excipient" means a pharmacologically inactive pharmaceutically acceptable compound added to a mucoadhesive composition of the invention. The ingredient or excipient does not have any pharmacological properties.

"Rapid delivery" means initial immediate rapid release and delivery of the components from the composition. The rapid delivery is typically followed by a time-dependent reduction in release of the components from the composition or device and delivery of the drug to the plasma/uterine wall tissues (or gastrointestinal tract, where appropriate).

"Controlled delivery" means a release wherein the active agent is released from the material in a predesigned manner. The release of the active agent may be constant over a long period, it may be cyclic over a long period, or it may be triggered by the environment or other external events.

"Continuous delivery" means continuous and uninterrupted release of the components from the formulation or device and delivering such components in a continuous manner. Continuous delivery may be preceded by the rapid delivery.

"Pulsed delivery" means a release and delivery of the components in intermittent intervals. Such pulsed delivery may be provided, for example, by formulating the composition in individual layers interspaced with inactive layers of dissolvable coatings or by using different pharmaceutical ingredients.

Seminal Fluid Cytokine Analysis

Sexually mature CD1 male mice (n=20) and Wistar rats (n=20) were sacrificed and seminal fluid collected from the seminal glands post mortem, a post mortem approach was chosen to avoid collecting samples by electroejaculation since semen quality is variable by this method, and because the samples coagulate rapidly, making analysis problematic. Seminal vesicle sampling is ideal as the fluid (rather than that of the accessory glands) contains the maternal tract immunomodulatory factors investigated and because coagulating gland secretions can more easily be avoided.

Seminal fluid samples were weighed individually, suspended in phosphate buffered saline (PBS) supplemented with 0.5% bovine serum albumin (BSA), and weighed again. By inference to standard weight:volume ratio of murine seminal fluid, it was possible to determine the original volume isolated and the dilution factor introduced by the PBS. This step was necessary because the fluid is too viscous to be pipetted accurately. Samples were spun and the supernatant frozen at −80° C. until analysed simultaneously for the following 23 cytokines: interleukin (IL)-1α, IL-2, IL-3, IL-4, IL-5, IL-6, IL-9, IL-10, IL-12 (p40), IL-12 (p70), IL-13, IL-17, eotaxin, granulocyte-colony stimulating factor (G-CSF), granulocyte macrophage-colony stimulating factor (GM-CSF), interferon (IFN)-γ, keratinocyte-derived chemokine (KC), monocytes chemotactic protein (MCP)-1, macrophage inhibitory protein (MIP)-1α, MIP-1β, regulated upon activation normal T cell expressed and secreted (RANTES) and tumour necrosis factor (TNF)-α. This was achieved by custom 23-plex fluid-phase immunoassay kits run on a Luminex-100™ equipped with StarStation™ software. Serum diluent was used in all cases to avoid false positive/negatives and dilution adjusted to 1:1 in order to maximise sensitivity to baseline levels. Similar analysis was performed on rat seminal fluid.

EXAMPLE 1

Table 2 below shows a variety of cytokines analyzed and measured in mouse seminal fluid. Eotaxin and RANTES appear to be the predominant cytokines present, with levels above 500 pg/ml. IL-9, TNF-α and MIP-1a had levels above 100 pg/ml whereas several cytokines such as G-CSF and IFN-γ had levels between 50-100 pg/ml and several others such as IL-13 and TGF-β had levels below 50 pg/ml.

TABLE 2

| Mouse | Mean | SEM |
|---|---|---|
| IL-1α | 8.19 | 1.96 |
| IL-1β | 87.48 | 9.04 |
| IL-2 | 3.03 | 0.49 |
| IL-3 | 0.35 | 0.04 |
| IL-4 | 0.11 | 0.01 |
| IL-5 | 0.56 | 0.07 |
| IL-6 | 3.63 | 0.44 |
| IL-9 | 135.14 | 33.47 |
| IL-10 | 19.95 | 3.36 |
| IL-12 p40 | 5.25 | 0.53 |
| IL-12 p70 | 10.91 | 1.08 |
| IL-13 | 20.64 | 1.86 |
| IL-17 | 5.10 | 0.90 |
| Eotaxin | 857.22 | 73.85 |
| G-CSF | 45.03 | 3.33 |
| GM-CSF | 4.16 | 0.39 |
| IFN-γ | 46.38 | 3.95 |
| KC | 37.17 | 3.56 |
| MCP-1 | 30.23 | 2.65 |
| MIP-1α | 114.32 | 8.31 |
| MIP-1β | 6.68 | 1.36 |
| RANTES | 618.62 | 84.17 |
| TNF-α | 102.27 | 9.11 |
| TGF-β | 27.63 | 6.54 |

Table 3 below shows a variety of cytokines analyzed and measured in rat seminal fluid. RANTES appears to be the predominant cytokine present. Of the cytokines analyzed only RANTES and GRO/KC had levels above 200 pg/ml. IL-10 and IL-6 had levels above 100 pg/ml whereas several cytokines such as MCP-1 had levels between 50-100 pg/ml and several others such as IL-17 had levels below 50 pg/ml.

TABLE 3

| Rat | Mean | SEM |
|---|---|---|
| IL-1α | 3.28 | 0.97 |
| IL-1β | 20.41 | 0.84 |
| IL-2 | 29.11 | 3.40 |
| IL-4 | 20.17 | 1.13 |
| IL-5 | 9.58 | 0.95 |
| IL-6 | 149.17 | 1.13 |
| IL-9 | 54.56 | 0.84 |
| IL-10 | 114.89 | 1.45 |
| IL-12 p70 | 55.14 | 4.31 |
| IL-13 | 8.29 | 1.35 |
| IL-17 | 15.80 | 1.11 |
| IL-18 | 6.66 | 0.89 |
| TNF-α | 2.27 | 0.16 |
| IFN-γ | 2.93 | 0.39 |
| Eotaxin | 34.84 | 1.45 |
| GCSF | 1.51 | 0.07 |
| GMCSF | 40.53 | 2.10 |
| MCP-1 | 61.56 | 2.21 |
| LEPTIN | 43.69 | 2.61 |
| MIP-1α | 0.13 | 0.02 |
| IP-10 | 4.24 | 0.34 |
| GRO/KC | 228.00 | 2.10 |
| RANTES | 287.31 | 2.21 |
| VEGF | 0.00 | 0.00 |
| TGF-β | 0.00 | 0.00 |

EXAMPLE 2

Eotaxin and RANTES appear to be the predominant cytokines each being present in an amount of more than 500pg/ml (see Tables 1 and 2). The cytokines IL-1α, IL-6, IL-10, IL-12 (p40), IL-12 (p70), GM-CSF and MIP-1β were present at levels below 20 pg/ml and cytokines IL-1β, IL-9, 1L-13, G-CSF, TNF-α, MCP-1, KC, MIP-1α and IFN-γ were present at levels above 20 and below 150 pg/ml. However, as stated hereinbefore the level of cytokines present does not necessarily correlate with the effect or potency.

Based on these analyses, a solution of cell culture-tested recombinant mouse cytokines was made up in PBS using recombinant cytokines at the concentrations found in seminal fluid (Table 3). This was stored at −80° C. until required for imbibing the pessary.

TABLE 4

Cytokine Concentrations in utero in a Mouse Pessary Preparation once solubilised.

| Cytokine | Pessary solution concentration (pg/ml) |
|---|---|
| IL-1α | 8.19 |
| IL-1β | 87.48 |
| IL-6 | 3.63 |
| IL-9 | 135.14 |
| IL-10 | 19.95 |
| IL-12 (p40) | 5.25 |
| IL-12 (p70) | 10.91 |
| IL-13 | 20.64 |
| G-CSF | 45.03 |
| GM-CSF | 4.16 |
| TNF-α | 102.27 |
| MCP-1 | 30.23 |
| RANTES | 618.62 |
| Eotaxin | 857.22 |
| KC | 37.17 |
| MIP-1α | 114.32 |
| MIP-1β | 6.68 |
| IFN-γ | 46.38 |

EXAMPLE 3

Additional formulation components of pessaries for laboratory animals was dictated principally by toxicity (in case of accidental ingestion), palatability (to dissuade ingestion) and impact on luminal pH (the bioactivity of certain cytokines is promoted by vaginal pH). The size and shape of the pessaries is largely determined by the species for which their use is intended. For example, pessaries of approximately 4 mm in diameter are particularly suitable for mice since the size has been determined as appropriate for insertion without undue discomfort and is also of a suitable size to be retained in the vaginal vestibule. Larger laboratory animals or indeed larger breeds of mice may necessitate larger pessaries. Pessaries were made from laser-etched nylon at a setting of between 5-10 Watts, use of this technique makes it possible to manipulate porosity (which facilitates 'loading') and overall shape and dimensions. It is envisaged that pessaries will be provided in a range of sizes and that the stalks may be snapped off from a central holding unit for use as desired and that a range of different sizes of pessaries may be provided to the user. Pessaries are prepared for use by soaking them overnight in 500 µl of 100 times the concentration of cytokine solution so as to load the pessaries with the necessary active agents to guarantee a seminal fluid like final concentration in the maternal reproductive tract. A pessary head is then removed from the stalk and inserted by means a suitable device directly into the mouse vagina. The pessary is then left in the mouse vagina for a period of time and then it is either removed at the time of embryo transfer when the animals are anaesthetised, or it self-dissolves or the pessary self ejects once the active ingredients have been absorbed.

It will be appreciated that the above embodiment is only one example of a means of delivering the compositions of the present invention and that the pessary may be in the form of a slow or fast melt wax type formulation and that the method of delivering the compositions of the present invention may vary from species to species. The delivery means may also be in the form of a biodegradable product and for example, in humans a vaginal sponge may be a more convenient method of delivering the compositions.

EXAMPLE 4

Embryo transfers into CD1 mice were investigated using the following protocol and combinations of cytokines.

Embryos were treated using M2 which is a common media for in vitro culture of pre-implantation stage embryos. M2 is a modified Krebs-Ringer bicarbonate solution and was used with HEPES for embryo transfer. However, if embryos were kept for any length of time (>4 embryo transfers time), they were transferred into a dish containing bicarbonate-buffered KSOM+Eagle's mix (amino acids)+1 mg/ml BSA and kept under 5% CO2 in an 37° C. incubator. Mice donors are approximately 4-6 weeks of age and recipients are approximately 6-10 weeks of age. Specific weight ranges were selected as weight is an important factor to consider and mice should be 20-30 gm, as less than 20 gm and they may not support pregnancy and greater than 30 gm and the abdominal fat present will make embryo transfer more difficult.

Pessaries were inserted by holding the females in scruff and allowing them to calm/relax, then 35 µl of the flush fluid is collected into a narrow-tipped Pasteur pipette and the fluid is flushed into the vagina. Fluid is flushed and collected 4-5 times (ending on a flush). The pessary is then inserted by hand after flush, with mouse still in scruff. The tail on the pessary is used to push the pessary to the other side of the vaginal muscles and it can be felt when the pessary will not go any further. Pessary retention is often short in some animals and is only monitored during the time taken to insert all pessaries on the day.

Females are then returned to home cages with cage mates following embryo transfer. Surgery clips are removed 5-7 days post-surgery. When checking for implantations (not live births), females are sacrificed 10 days after the embryo transfer and foetus number present in the uterine horn is documented. At this stage, resorptions can be seen (smaller and different in colour to other foetuses) and are also recorded. For live births, females are group housed until approximately 18 days into pregnancy. They may be visually monitored for signs of pregnancy and they are weighed before embryo transfer and then weekly until birth. This helps to identify whether the female may have lost her litter or destroyed it before the pups were seen. Pup body mass is recorded at 7 days of age and at weaning (20-21 days). Pups are also sexed at weaning.

Table 5 below shows the protocol of days 1 to 6.

| Day | Donor females | Recipient females | Comments |
|---|---|---|---|
| 1 | Male bedding | | |
| 2 | PMSG | Male bedding | 5 IU |
| 3 | | PMSG | 2.5 IU |
| 4 | hCG and mate with stud males | | 5 IU |
| 5 | Plug check | hCG and mate with vasectomised males/ give pessary treatment | 2.5 IU |
| 6 | Harvest embryos | Plug check those mated with vasectomised males Embryo transfers | 15 embryos transferred unilaterally into oviduct by laparotomy |

The treatment groups were as follows, vasectomised males (Vsx) and pessaries consisting of a mixture MIP, IL-12, IL-13, G-CSF and GM-CSF (5 mix) plus other pessaries of the five cytokines as solo components (not all data shown) and other pessaries of combinations, GM-CSF with IL-12, GM-CSF with IL-12 and IL-13 and GM-CSF with IL-12 and MIP. The total successful pregnancies with embryo transfer were recorded. Table 6 shows the treatment (cytokine pessaries) versus successful pregnancy outcome.

TABLE 6

| Treatment | Successful/total |
|---|---|
| Vsx | 1/3 |
| 5 mix | 1/5 |
| IL-12 | 3/5 |
| GM-CSF + IL-12 | 4/5 |
| GM-CSF + IL-12 + IL-13 | 2/5 |
| GM-CSF + IL-12 + MIP | 0/5 |

This data supports the present invention in showing that IL-12 alone or in combination can be used to successfully increase the rate of implantation rate as compared to prior art methods.

Throughout the description and claims of this specification, the words "comprise" and "contain" and variations of them mean "including but not limited to", and they are not intended to (and do not) exclude other moieties, additives, components, integers or steps. According to further embodiments of the present invention, the compositions and methods described herein may also consist essentially of or consist of components and/or steps recited therein. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with, this application and which are open to public inspection with this specification, and the contents of all such papers and documents are incorporated herein by reference.

The invention claimed is:

1. A composition of matter for use in improving pregnancy rates in females prior to implantation of an embryo or prior to insemination, the composition consisting essentially of recombinant IL-12 and recombinant GM-CSF, wherein the composition is configured to release the recombinant IL-12 and recombinant GM-CSF in situ in a vagina within a physiological concentration range as corresponding IL-12 and GM-CSF found in seminal fluid of a fertile male.

2. The composition according to claim 1, wherein the recombinant IL-12 is either IL-12p40 or IL-12p70.

3. The composition according to claim 1, wherein the recombinant IL-12 and recombinant GM-CSF are active ingredients.

4. A pessary for transmucosal vaginal delivery comprising the composition according to claim 1 for use in improving pregnancy rates.

5. The pessary according to claim 4 for promoting uterine receptivity in a rodent.

6. The pessary according to claim 5, wherein the rodent is a mouse or rat.

7. A pharmaceutical composition for use in improving pregnancy rates in females prior to implantation of an embryo or prior to insemination, the pharmaceutical composition consisting essentially of recombinant IL-12 and recombinant GM-CSF, and wherein the pharmaceutical composition is a vaginal insert, and wherein the pharmaceutical composition is configured to release the recombinant IL-12 and recombinant GM-CSF in situ in a vagina within a physiological concentration range as corresponding IL-12 and GM-CSF found in seminal fluid of a fertile male.

8. The pharmaceutical composition according to claim 7, wherein the recombinant IL-12 and recombinant GM-CSF are configured to be released in situ either above or within their approximate physiological ranges as found in seminal fluid of a fertile male.

9. The pharmaceutical composition according to claim 7, wherein the vaginal insert is a vaginal capsule, vaginal gel, vaginal tablet, vaginal powder, vaginal solution, vaginal pessary, vaginal cup, vaginal sponge, vaginal aerosol or vaginal foam or spray.

10. The pharmaceutical composition according to claim 7, wherein the pharmaceutical composition is a rapid delivery, controlled delivery, continuous delivery or pulsed delivery formulation.

11. A method of improving pregnancy rates comprising exposing the vaginal mucosa to a composition according to claim 1, the pharmaceutical composition of claim 7, or the pessary of claim 4, the method comprising:
  (i) introducing at least one vaginal delivery vehicle comprising the composition according to claim 1, the pharmaceutical composition of claim 7, or the pessary of claim 4, into the vagina of a female, wherein the recombinant IL-12 and recombinant GM-CSF are active ingredients;
  (ii) allowing a sufficient period of time to elapse to allow the active components ingredients of the at least one vaginal delivery vehicle to be released and to penetrate into the vagina and be absorbed transmucosally and/or diffuse and/or be transported into the uterus; and
  (iii) inseminating the female by either mating with a male or by artificial insemination, donor gametes or introducing an embryo or other allograft into the uterus for implantation.

12. The method according to claim 11, wherein steps (ii) and (iii) are performed simultaneously or in close chronological sequence.

13. A kit comprising a vaginal delivery vehicle comprising the composition according to claim 1, the pharmaceutical composition of claim 7, or the pessary of claim 4, and an apparatus for inserting the vaginal delivery vehicle when contained in the kit into the vagina of a recipient female.

14. A composition of matter for use in improving pregnancy rates in females prior to implantation of an embryo or prior to insemination, the composition consisting essentially of any one, two, or three of recombinant TGF$\beta$, recombinant Eotaxin and recombinant RANTES, wherein the composition-releases the any one, two, or three of the recombinant TGF$\beta$ recombinant Eotaxin and recombinant RANTES in situ in a vagina within a physiological concentration range as corresponding TGF$\beta$, Eotaxin and RANTES found in seminal fluid of a fertile male.

15. A pharmaceutical composition of matter for use in improving pregnancy rates in females prior to implantation of an embryo or prior to insemination, the pharmaceutical composition consisting essentially of any one, two, or three of recombinant TGF$\beta$, recombinant Eotaxin and recombinant RANTES, wherein the pharmaceutical composition is configured to release the any one, two, or three of the recombinant TGF$\beta$, recombinant Eotaxin and recombinant RANTES in situ in a vagina within a physiological concentration range as corresponding TGF$\beta$, Eotaxin and RANTES found in seminal fluid of a fertile male.

* * * * *